US009745316B2

(12) United States Patent
Tavares

(10) Patent No.: US 9,745,316 B2
(45) Date of Patent: Aug. 29, 2017

(54) LACTAM KINASE INHIBITORS

(71) Applicant: G1 Therapeutics, Inc., Chapel Hill, NC (US)

(72) Inventor: Francis Xavier Tavares, Durham, NC (US)

(73) Assignee: G1 Therapeutics, Inc., Chapel Hill, NC (US)

(*) Notice: Subject to any disclaimer, the term of this patent is extended or adjusted under 35 U.S.C. 154(b) by 0 days.

(21) Appl. No.: 14/982,443

(22) Filed: Dec. 29, 2015

(65) Prior Publication Data

US 2016/0108054 A1    Apr. 21, 2016

Related U.S. Application Data

(60) Division of application No. 14/498,796, filed on Sep. 26, 2014, now Pat. No. 9,260,442, which is a continuation of application No. PCT/US2013/033971, filed on Mar. 27, 2013.

(60) Provisional application No. 61/617,657, filed on Mar. 29, 2012.

(51) Int. Cl.
  *C07D 487/14* (2006.01)
  *C07D 413/12* (2006.01)
  *C07D 413/10* (2006.01)
  *A61K 31/4985* (2006.01)
  *A61K 31/407* (2006.01)
  *A61K 31/5377* (2006.01)
  *C07D 498/14* (2006.01)
  *C07D 487/20* (2006.01)

(52) U.S. Cl.
  CPC ......... *C07D 487/14* (2013.01); *C07D 487/20* (2013.01); *C07D 498/14* (2013.01)

(58) Field of Classification Search
  CPC .. C07D 487/14; C07D 413/12; C07D 413/10; A61K 31/498; A61K 31/407; A61K 31/5377; A61K 31/4985
  USPC ................ 544/251, 252, 115; 548/428, 429; 514/267, 250, 233.2, 411
  See application file for complete search history.

(56) References Cited

U.S. PATENT DOCUMENTS

| | | | |
|---|---|---|---|
| 6,962,993 | B2 | 11/2005 | Blumenkopf et al. |
| 7,345,171 | B2 | 3/2008 | Beylin et al. |
| 8,598,186 | B2 | 12/2013 | Tavares et al. |
| 8,598,197 | B2 | 12/2013 | Tavares et al. |
| 8,691,830 | B2 | 4/2014 | Tavares et al. |
| 8,822,683 | B2 | 9/2014 | Tavares et al. |
| 8,829,012 | B2 | 9/2014 | Tavares et al. |
| 9,102,682 | B2 | 8/2015 | Tavares et al. |
| 9,260,442 | B2 | 2/2016 | Tavares |
| 2004/0236084 | A1 | 11/2004 | Biwersi et al. |
| 2014/0271460 | A1 | 9/2014 | Sharpless et al. |
| 2014/0271466 | A1 | 9/2014 | Sharpless et al. |
| 2014/0274896 | A1 | 9/2014 | Sharpless et al. |
| 2014/0275066 | A1 | 9/2014 | Sharpless et al. |
| 2014/0275067 | A1 | 9/2014 | Sharpless et al. |
| 2015/0246925 | A1 | 9/2015 | Tavares et al. |
| 2015/0246926 | A1 | 9/2015 | Tavares et al. |
| 2016/0045509 | A1 | 2/2016 | Strum et al. |

FOREIGN PATENT DOCUMENTS

| | | |
|---|---|---|
| JP | 2007-530425 | 11/2007 |
| WO | WO 98/33798 | 8/1998 |
| WO | WO 99/15500 A1 | 4/1999 |
| WO | WO 03/062236 A1 | 7/2003 |
| WO | WO 2005/005426 | 1/2005 |
| WO | WO 2005/040166 A1 | 5/2005 |
| WO | WO 2005/052147 A2 | 6/2005 |
| WO | WO 2005/105213 A2 | 11/2005 |
| WO | WO 2006/074985 | 7/2006 |
| WO | WO 2006/127587 A1 | 11/2006 |
| WO | WO 2007/025090 A2 | 3/2007 |
| WO | WO 2007/048847 A2 | 5/2007 |
| WO | WO 2007/065820 A1 | 6/2007 |
| WO | WO 2009/003003 A2 | 12/2008 |
| WO | WO 2009/085185 A1 | 7/2009 |
| WO | WO 2010/020675 A1 | 2/2010 |
| WO | WO 2010/039997 A2 | 4/2010 |
| WO | WO 2010/051127 A2 | 5/2010 |
| WO | WO 2010/132725 A2 | 11/2010 |
| WO | WO 2011/101409 | 8/2011 |
| WO | WO 2011/103485 A1 | 8/2011 |
| WO | WO 2012/061156 | 10/2012 |
| WO | WO 2013/148748 A1 | 10/2013 |
| WO | WO 2013/163239 A1 | 10/2013 |
| WO | WO 2014/144326 A1 | 9/2014 |
| WO | WO 2014/144596 A2 | 9/2014 |
| WO | WO 2014/144740 A2 | 9/2014 |
| WO | WO 2014/144847 A2 | 9/2014 |

(Continued)

OTHER PUBLICATIONS

Chu et al. "Discovery of [4-Amino-2-(1-methanesulfonylpiperidin-4-ylamino)pyrimidin-5-yl](2,3-difluoro-6-methoxyphenyl)methanone (R547), a potent and selective cyclin-dependent kinase inhibitor with significant in vivo antitumor activity" J Med Chem, Nov. 2, 2006; 49(22): 6549-6560.

Goldberg et al. "Pyrazinoindolone inhibitors of MAPKAP-K2" Biogranic & Medicinal Chemistry Letters, Dec. 23, 2007, 18, 938-941.

Guillard et al., "Synthesis and biological evaluations of new pyrrolo[2,3-b]pyrimidine as SDI analogs" Heterocyles, 2008, vol. 75(5), pp. 1163-1189.

McInnes, C. "Progress in the evaluation of CDK inhibitors as anti-tumor agents" Drug Discov Today, Oct. 2008; 13(19-20): 875-881.

Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, vol. 135, Issue 8, pp. 1015-1022.

(Continued)

*Primary Examiner* — Alicia L Otton
*Assistant Examiner* — Sagar Patel
(74) *Attorney, Agent, or Firm* — Knowles Intellectual Property Strategies, LLC

(57) ABSTRACT

Compounds useful as kinase inhibitors are provided herein, as well as salts, pharmaceutical compositions, methods of medical treatment and methods of synthesis thereof.

20 Claims, No Drawings

(56) References Cited

FOREIGN PATENT DOCUMENTS

WO  WO 2015/061407  4/2015

OTHER PUBLICATIONS

Schonauer, K. and E. Zibral "Reactions with organophosphorus compounds, 50.: Trimethylsilylethoxymethylene triphenylphosphorane, a novel reagent for the homologation of carbonyl compounds." Tetrahedron Letters, 1983; 24: 573-576.

Shimamura, T. et al. "Identification of potent 5-pyrimidinyl-2-aminothiazole CDK4, 6 inhibitors with significant selectivity over CDK1, 2, 5, 7, and 9" Bioorg Med Chem Lett., Jul. 15, 2006; 16(14): 3751-3754.

Soni, R. et al. "Selective in vivo and in vitro effects of a small molecule inhibitor of cyclin-dependent kinase 4" J Natl Cancer Inst, Mar. 21, 2001; 93(6): 436-446.

Toogood, P. L. et al. "Discovery of a potent and selective inhibitor of cyclin-dependent kinase 4/6" J Med Chem, Apr. 7, 2005; 48(7): 2388-2406.

White, J.D. et al. "Transformations of Quinic Acid. Asymmetric Synthesis and Absolute Configuration of Mycosporin I and Mycosporin-gly" Journal of Organic Chemistry, 1995, vol. 60, Issue 12, pp. 3600-3611.

LACTAM KINASE INHIBITORS

CROSS-REFERENCE TO RELATED APPLICATIONS

This application is a divisional of U.S. application Ser. No. 14/498,796 filed Sep. 26, 2014, which is a continuation of PCT Application No. PCT/US2013/033971 filed Mar. 27, 2013, which claims the benefit of provisional U.S. Application No. 61/617,657 filed Mar. 29, 2012. The entirety of these applications is hereby incorporated by reference for all purposes.

FIELD OF THE INVENTION

The invention relates to novel compounds useful as kinase inhibitors in medicine.

BACKGROUND OF THE INVENTION

A protein kinase inhibitor is a type of enzyme inhibitor that specifically blocks the action of one or more protein kinases. Protein kinases are enzymes that add a phosphate ($PO_4$) group to a protein or other organic molecule, usually on the serine, threonine, or tyrosine amino acid. Hence, protein kinase inhibitors can be subdivided or characterized by the amino acids whose phosphorylation is inhibited: most kinases act on both serine and threonine, the tyrosine kinases act on tyrosine, and a number (dual-specificity kinases) act on all three. There are also protein kinases that phosphorylate other amino acids, including histidine kinases that phosphorylate histidine residues. Phosphorylation is a necessary step in some cancers and inflammatory diseases. Inhibiting the protein kinases can treat these diseases and protein kinase inhibitors are used as drugs. Literature on the use of kinases inhibitors in drug discovery includes "Targeting Protein Kinases for Cancer Therapy" by Mathew D. J et al, Publisher J. Wiley 2010 and also "Protein Kinases as Drug targets" Klebl et al. J. Wiley 2011.

SUMMARY OF THE INVENTION

Compounds of formulae (Q) and (QQ) are provided as part of the invention:

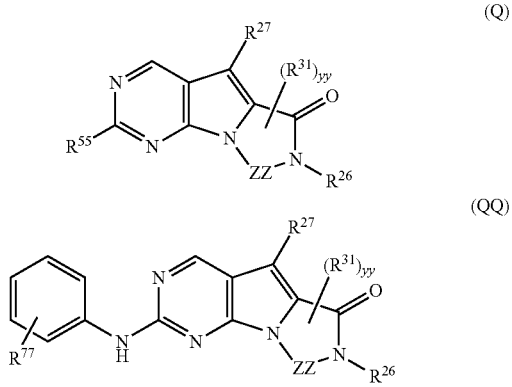

DETAILED DESCRIPTION OF THE INVENTION

A compound of the formulae (Q) or (QQ) above are part of the invention, wherein $R^{26}$ is H, $C_1$-$C_6$ alkyl, or haloalkyl, cycloalkyl or cycloalkyl containing one or more heteroatoms selected from N, O, and S;

each $R^{31}$ is independently aryl, alkyl, cycloalkyl or haloalkyl, wherein each of said alkyl, cycloalkyl and haloalkyl groups optionally includes O or N heteroatoms and two $R^{31}$s on adjacent ring atoms or on the same ring atom together with the ring atom(s) to which they are attached optionally form a 3-8-membered cycle;

yy is 0, 1, 2, 3 or 4;

ZZ is —$(CH_2)_{xx}$— wherein xx is 1, 2, 3 or 4 or —$O(CH_2)_{xx}$— wherein xx is 2, 3 or 4;

$R^{55}$ is $NHR^4$, $R^4$ is unsubstituted $C_1$-$C_8$ alkyl, cycloalkylalkyl, or -TT-RR, $C_1$-$C_8$ cycloalkyl or cycloalkyl containing one or more heteroatoms selected from N, O, and S, TT is an unsubstituted or substituted $C_1$-$C_8$ alkyl or $C_3$-$C_8$ cycloalkyl linker; and RR is a hydroxyl, unsubstituted or substituted $C_1$-$C_6$ alkoxy, amino, unsubstituted or substituted $C_1$-$C_6$ alkylamino, unsubstituted or substituted di-$C_1$-$C_6$ alkylamino, unsubstituted or substituted $C_6$-$C_{10}$ aryl, unsubstituted or substituted heteroaryl comprising one or two 5- or 6-member rings and 1-4 heteroatoms selected from N, O and S, unsubstituted or substituted $C_3$-$C_{10}$ carbocycle, or unsubstituted or substituted heterocycle comprising one or two 5- or 6-member rings and 1-4 heteroatoms selected from N, O and S;

$R^{77}$ is -(alkylene)$_m$-heterocyclo, -(alkylene)$_m$-heteroaryl, -(alkylene)$_m$-$NR^3R^4$, -(alkylene)$_m$-C(O)—$NR^3R^4$; -(alkylene)$_m$-O—$R^5$, -(alkylene)$_m$-S(O)$_n$—$R^5$, or -(alkylene)$_m$-S(O)$_n$—$NR^3R^4$ any of which may be optionally independently substituted with one or more $R^x$ groups as allowed by valance, and wherein two $R^x$ groups bound to the same or adjacent atoms may optionally combine to form a ring;

$R^3$ and $R^4$ at each occurrence are independently:
(i) hydrogen or
(ii) alkyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance, and wherein two $R^x$ groups bound to the same or adjacent atom may optionally combine to form a ring; or $R^3$ and $R^4$ together with the nitrogen atom to which they are attached may combine to form a heterocyclo ring optionally independently substituted with one or more $R^x$ groups as allowed by valance, and wherein two $R^x$ groups bound to the same or adjacent atoms may optionally combine to form a ring;

$R^5$ and $R^{5*}$ at each occurrence is:
(i) hydrogen, or
(ii) alkyl, alkenyl, alkynyl, cycloalkyl, heterocyclo, aryl, heteroaryl, cycloalkylalkyl, heterocycloalkyl, arylalkyl, or heteroarylalkyl any of which may be optionally independently substituted with one or more $R^x$ groups as allowed by valance;

$R^x$ at each occurrence is independently, halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, heterocycloalkyl, -(alkylene)$_m$-$OR^5$, -(alkylene)$_m$-O-alkylene-$OR^5$, -(alkylene)$_m$-S(O)$_n$—$R^5$, -(alkylene)$_m$-$NR^3R^4$, -(alkylene)$_m$-CN, -(alkylene)$_m$-C(O)—$R^5$, -(alkylene)$_m$-C(S)—$R^5$, -(alkylene)$_m$-C(O)—$OR^5$, -(alkylene)$_m$-O—C(O)—$R^5$, -(alkylene)$_m$-C(S)—$OR^5$, -(alkylene)$_m$-C(O)-(alkylene)$_m$-$NR^3R^4$, -(alkylene)$_m$-C(S)—$NR^3R^4$, -(alkylene)$_m$-N($R^3$)—C(O)—$NR^3R^4$, -(alkylene)$_m$-N($R^3$)—C(S)—$NR^3R^4$, -(alkylene)$_m$-N($R^3$)—C(O)—$R^5$, -(alkylene)$_m$-N($R^3$)—C(S)—$R^5$, -(alkylene)$_m$-O—C(O)—$NR^3R^4$, -(alkylene)$_m$-O—C(S)—$NR^3R^4$, -(alkylene)$_m$-$SO_2$—$NR^3R^4$, -(alkylene)$_m$-N($R^3$)—$SO_2$—$R^5$, -(alkylene)$_m$-N(R$^3$)—SO$_2$—NR$^3$R$^4$, -(alkylene)$_m$-N(R$^3$)—C(O)—OR$^5$)-(alkylene)$_m$-N(R$^3$)—C(S)—OR$^5$, or -(alkylene)$_m$-N(R$^3$)—SO$_2$—R$^5$; wherein:

said alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl groups may be further independently substituted with one or more -(alkylene)$_m$-CN, -(alkylene)$_m$-OR$^{5*}$, -(alkylene)$_m$-S(O)$_n$—R$^{5*}$, -(alkylene)$_m$-NR$^{3*}$R$^{4*}$, -(alkylene)$_m$-C(O)—R$^{5*}$, -(alkylene)$_m$-C(=S)R$^{5*}$, -(alkylene)$_m$-C(=O)OR$^{5*}$, -(alkylene)$_m$-OC(=O)R$^{5*}$, -(alkylene)$_m$-C(S)—OR$^{5*}$, -(alkylene)$_m$-C(O)—NR$^{3*}$R$^{4*}$, -(alkylene)$_m$-C(S)—NR$^{3*}$R$^{4*}$, -(alkylene)$_m$-N(R$^{3*}$)—C(O)—NR$^{3*}$R$^{4*}$, -(alkylene)$_m$-N(R$^{3*}$)—C(S)—NR$^{3*}$R$^{4*}$, -(alkylene)$_m$-N(R$^{3*}$)—C(O)—R$^{5*}$, -(alkylene)$_m$-N(R$^{3*}$)—C(S)—R$^{5*}$, -(alkylene)$_m$-O—C(O)—NR$^{3*}$R$^{4*}$, -(alkylene)$_m$-O—C(S)—NR$^{3*}$R$^{4*}$, -(alkylene)$_m$-SO$_2$—NR$^{3*}$R$^{4*}$, -(alkylene)$_m$-N(R$^{3*}$)—SO$_2$—R$^{5*}$, -(alkylene)$_m$-N(R$^{3*}$)—SO$_2$—NR$^{3*}$R$^{4*}$, -(alkylene)$_m$-N(R$^{3*}$)—C(O)—OR$^{5*}$, -(alkylene)$_m$-N(R$^{3*}$)—C(S)—OR$^{5*}$, or -(alkylene)$_m$-N(R$^{3*}$)—SO$_2$—R$^{5*}$, n is 0, 1 or 2, and
m is 0 or 1; and
R$^{3*}$ and R$^{4*}$ at each occurrence are independently:
(i) hydrogen or
(ii) alkyl, alkenyl, alkynyl cycloalkyl, heterocyclo, aryl, heteroaryl, cycloalkylalkyl, heterocycloalkyl, arylalkyl, or heteroarylalkyl any of which may be optionally independently substituted with one or more R$^x$ groups as allowed by valance; or R$^{3*}$ and R$^{4*}$ together with the nitrogen atom to which they are attached may combine to form a heterocyclo ring optionally independently substituted with one or more R$^x$ groups as allowed by valance; and
R$^{27}$ is -(alkylene)$_m$-C$_3$-C$_8$ cycloalkyl, -(alkylene)$_m$-aryl, -(alkylene)$_m$-heterocyclo, -(alkylene)$_m$-heteroaryl, -(alkylene)$_m$-NR$^3$R$^4$, -(alkylene)$_m$-C(O)—NR$^3$R$^4$; -(alkylene)$_m$-O—R$^5$, -(alkylene)$_m$-S(O)$_n$—R$^5$, or -(alkylene)$_m$-S(O)$_n$—NR$^3$R$^4$ any of which may be optionally independently substituted with one or more R$^x$ groups as allowed by valance, and wherein two R$^x$ groups bound to the same or adjacent atoms may optionally combine to form a ring, providing that in (Q), R$^{27}$ may also be H, C$_1$-C$_3$ alkyl or haloalkyl, or a pharmaceutically acceptable salt thereof. In some specific cases, aryl, such as phenyl, or heteroaryl can be ortho alkyl, cycloalkyl, halo, haloalkyl, thioalkyl, sulfonylalkyl, or aminodialkyl. Aryl and heteroaryl could also be ortho-disubstituted with alkyl, cycloalkyl, halo, haloalkyl, thioalkyl, sulfonylalkyl, or aminodialkyl as allowed by valence. Aryl and heteroaryl could also be meta or para substituted with alkyl, cycloalkyl, haloalkyl, halo, haloalkyl, thioalkyl, sulfonylalkyl, or aminoalkyl.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology The term "alkyl," either alone or within other terms such as "haloalkyl" and "alkylamino," embraces linear or branched radicals having one to about twelve carbon atoms. "Lower alkyl" radicals have one to about six carbon atoms. Examples of such radicals include methyl, ethyl, n-propyl, isopropyl, n-butyl, isobutyl, sec-butyl, tert-butyl, pentyl, isoamyl, hexyl and the like.

The term "alkylene" embraces bridging divalent alkyl radicals. Examples include methylene, ethylene, propylene, isopropylene and the like.

"Alkenyl" embraces linear or branched radicals having at least one carbon-carbon double bond of two to about twelve carbon atoms. "Lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl," embrace radicals having "cis" and "trans" orientations, or alternatively, "E" and "Z" orientations.

"Alkynyl" denotes linear or branched radicals having at least one carbon-carbon triple bond and having two to about twelve carbon atoms. "Lower alkynyl" radicals may have two to about six carbon atoms. Examples of such radicals include propargyl, butynyl, and the like.

Alkyl, alkenyl, and alkynyl radicals may be optionally substituted with one or more functional groups such as halo, hydroxy, nitro, amino, cyano, haloalkyl, aryl, heteroaryl, heterocyclo, etc.

"Alkylamino" embraces "N-alkylamino" and "N,N-dialkylamino" where amino groups are independently substituted with one alkyl radical and with two alkyl radicals, respectively. "Lower alkylamino" radicals have one or two alkyl radicals of one to six carbon atoms attached to a nitrogen atom. Suitable alkylamino radicals may be mono or dialkylamino such as N-methylamino, N-ethylamino, N.N-dimethylamino, N,N-diethylamino and the like.

"Halo" means halogens such as fluorine, chlorine, bromine or iodine atoms.

"Haloalkyl" embraces radicals wherein any one or more of the alkyl carbon atoms is substituted with one or more halo as defined above. Examples include monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

"Perfluoroalkyl" means alkyl having all hydrogen atoms replaced with fluoro atoms, eg trifluoromethyl and pentafluoroethyl.

"Aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 or more substituents such as lower alkyl, hydroxyl, halo, haloalkyl, nitro, cyano, alkoxy, lower alkylamino, and the like. An aryl group may be optionally substituted with one or more functional groups such as halo, hydroxy, nitro, amino, cyano, haloalkyl, aryl, heteroaryl, heterocyclo and the like.

"Heterocyclyl" (or "heterocyclo") embraces saturated, and partially saturated heteroatom-containing ring radicals, where the heteroatoms may be selected from nitrogen, sulfur and oxygen.

Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino, lower alkylamino, and the like. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl, dihydrothiazolyl, and the like.

Particular examples of partially saturated and saturated heterocyclo groups include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like. Heterocyclo groups also includes radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl, e.g., tetrazolo[1,5-b]pyridazinyl; unsaturated condensed heterocyclic group containing 1 to 2 oxygen atoms and 1 to 3 nitrogen atoms, e.g. benzoxazolyl, benzoxadiazolyl; unsaturated condensed heterocyclic group containing 1 to 2 sulfur atoms and 1 to 3 nitrogen atoms, e.g., benzothiazolyl, benzothiadiazolyl; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl].

The term "heteroaryl" denotes aryl ring systems that contain one or more heteroatoms selected from the group O, N and S, wherein the ring nitrogen and sulfur atom(s) are optionally oxidized, and nitrogen atom(s) are optionally quarternized. Examples include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heteroarylalkyl" denotes alkyl radicals substituted with a heteroaryl group. Examples include pyridylmethyl and thienylethyl.

The term "sulfonyl", whether used alone or linked to other terms such as alkylsulfonyl, denotes respectively divalent radicals —$SO_2$—.

The terms "carboxy" or "carboxyl", whether used alone or with other terms, such as "carboxyalkyl", denotes —C(O)—OH.

The term "carbonyl", whether used alone or with other terms, such as "aminocarbonyl", denotes —C(O)—.

"Aminocarbonyl" denotes an amide group of the formula —C(O)—$NH_2$.

"Heterocycloalkyl" embraces heterocyclic-substituted alkyl radicals. Examples include piperidylmethyl and morpholinylethyl.

"Arylalkyl" embraces aryl-substituted alkyl radicals. Examples include benzyl, diphenylmethyl and phenylethyl. The aryl in said aralkyl may be additionally substituted with halo, alkyl, alkoxy, halkoalkyl and haloalkoxy.

"Cycloalkyl" includes saturated carbocyclic groups of 3 to 10 carbons. Lower cycloalkyl groups include $C_3$-$C_6$ rings. Examples include cyclopentyl, cyclopropyl, and cyclohexyl. Cycloalkyl groups may be optionally substituted with one or more functional groups such as halo, hydroxy, nitro, amino, cyano, haloalkyl, aryl, heteroaryl, heterocyclo and the like. "Cycloalkylalkyl" embraces cycloalkyl-substituted alkyl radicals. "Lower cycloalkylalkyl" radicals are cycloalkyl radicals attached to alkyl radicals having one to six carbon atoms. Examples of include cyclohexylmethyl. The cycloalkyl in said radicals may be additionally substituted with halo, alkyl, alkoxy and hydroxy.

"Cycloalkenyl" includes carbocyclic groups having one or more carbon-carbon double bonds including "cycloalkyldienyl" compounds. Examples include cyclopentenyl, cyclopentadienyl, cyclohexenyl and cycloheptadienyl.

"Comprising" is meant to be open ended, including the indicated component but not excluding other elements.

"Oxo" as used herein contemplates an oxygen atom attached with a double bond. "Nitro" as used herein contemplates —$NO_2$. "Cyano" as used herein contemplates —CN.

Particular values of $R^{26}$ are H, methyl, ethyl, n-propyl, cyclopropyl and sec-butyl; of $R^{31}$ are methyl, ethyl, n-propyl, iso-propyl, cyclopropyl, cyclobutyl, cyclopentyl, and cyclohexyl; of yy are 0, 1 and 2; of ZZ are —$CH_2$—, —$CH_2CH_2$—, —$C(CH_3)_2CH_2$— reading from left to right or right to left and —$CH_2$CH(spriocyclopentyl or spriocyclohexyl)- reading from left to right or right to left in the depicted formulae; of $R^{55}$ are cis or trans 4-hydroxycyclohexylamino, cyclohexyl- or cyclopenylamino and straight chain $C_1$-$C_8$ alkylamino; of $R^{77}$ are 1-morpholino, 2-methyl-1-morpholino and 2,6-dimethyl-1-morpholino; of $R^3$ and $R^4$ are H, methyl, ethyl, cyclohexyl and $R^3$ and $R^4$ are alkyl and combine to form a 5- or 6-membered ring; of $R^5$ and $R^{5*}$ are H, methyl, ethyl, n-propyl and cyclopropylmethyl; of $R^x$ are chloro, methyl, ethyl and cyclopentyl; of $R^{3*}$ and $R^{4*}$ are H, methyl, ethyl, iso-propyl, n-buten-2-yl and phenyl; and of $R^{27}$ are H, phenyl, ortho-methylphenyl, ortho,ortho-dimethylphenyl, para-ethylphenyl and ortho, para-dichlorophenyl.

The disclosed compounds can be made by the following general schemes:

US 9,745,316 B2
Scheme 1
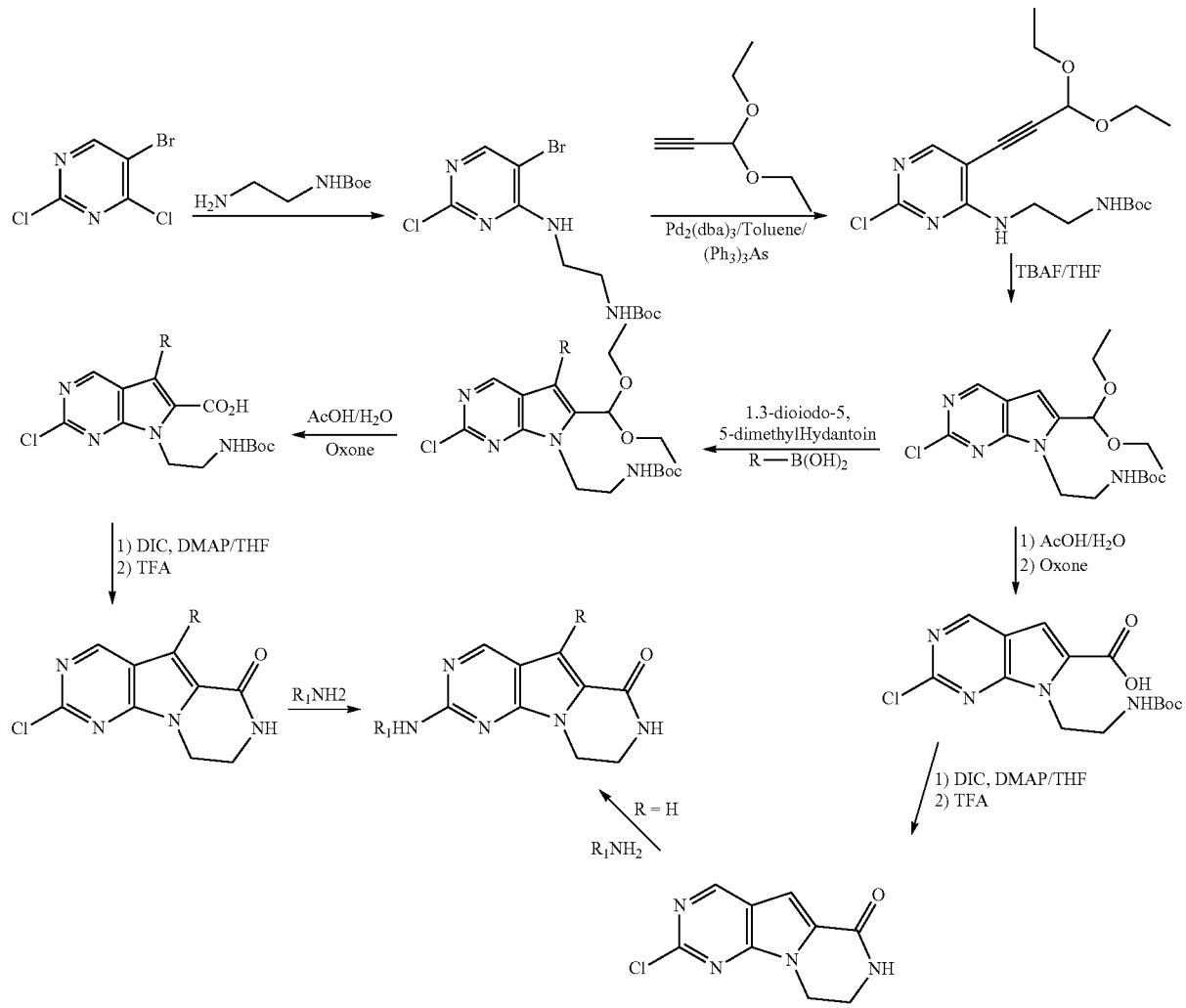
Scheme 2
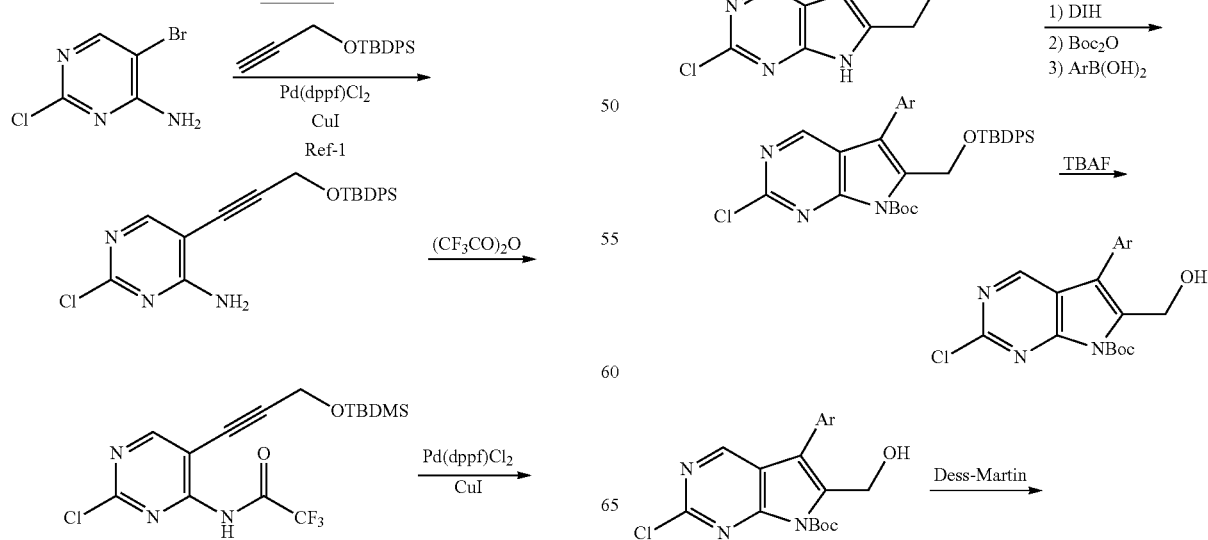

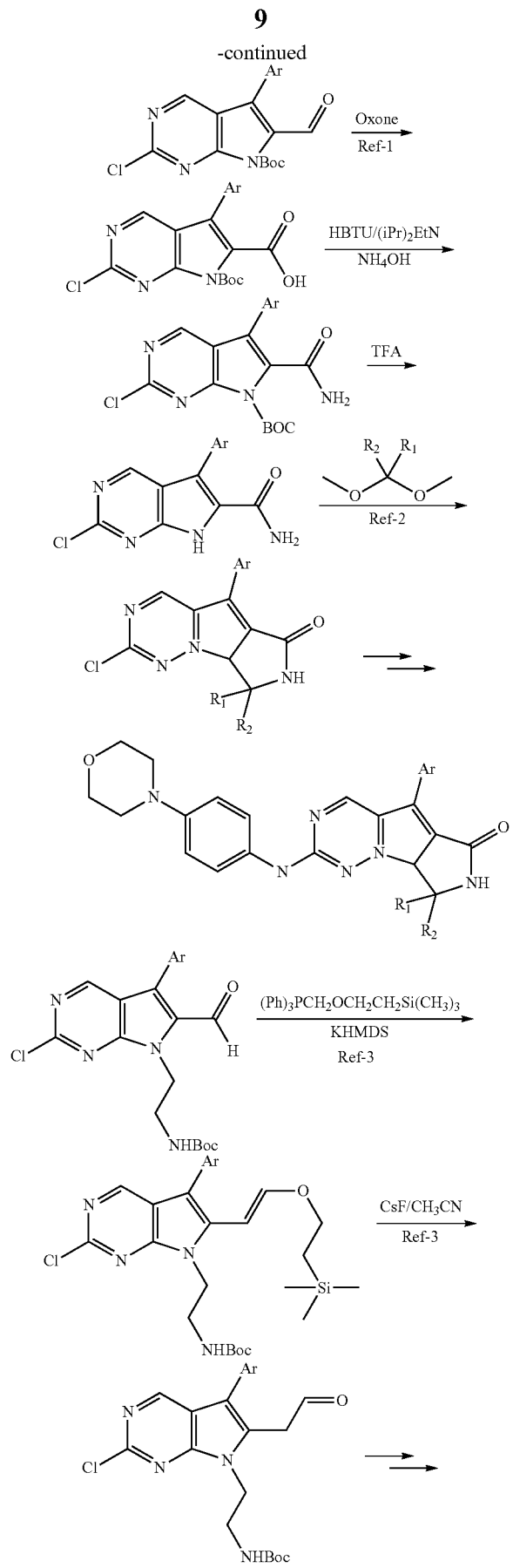

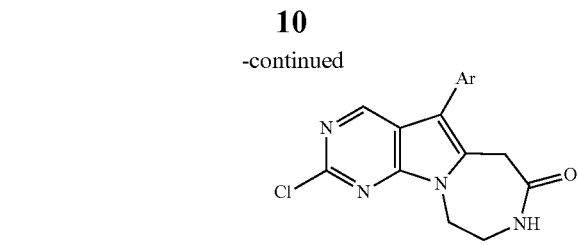

DIH = 1,3-Diiodo-3,3-dimethyl-hydantion

In Scheme 2, Ref-1 is WO 2010/020675 A1; Ref-2 is WO 2005/040166 A1; and Ref-3 is Schoenauer, K and Zbiral, E. *Tetrahedron Letters* 1983, 24, 573.

EXAMPLES tert-butyl N-[2-[(5-bromo-2-chloro-pyrimidin-4-yl)amino]ethyl]carbamate

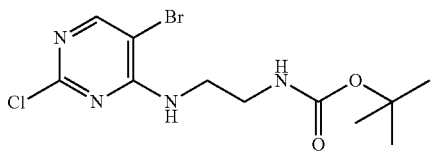 [SMILES: CC(C)(C)OC(=O)NCCNc1nc(Cl)ncc1Br]

To a solution of 5-bromo-2,4-dichloropyrimidine 12.80 g (0.054 mole) in ethanol 250 mL was added Hunig's base 12.0 mL followed by the addition of a solution of N-(tert-butoxycarbonyl)-1,2-diaminoethane 10 g (0.0624 mole) in 80 mL ethanol. The contents were stirred overnight for 20 hrs. The solvent was evaporated under vacuum. Ethyl acetate (800 mL) and water (300 mL) was added and the layers separated. The organic layer was dried with magnesium sulfate and then concentrated under vacuum. Column chromatography on silica gel using hexane/ethyl acetate (0-60%) afforded tert-butyl N-[2-[(5-bromo-2-chloro-pyrimidin-4-yl)amino]ethyl]carbamate. LCMS (ESI) 351 (M+H).

tert-butyl N-[2-[[2-chloro-5-(3,3-diethoxyprop-1-ynyl)pyrimidin-4 yl]amino]ethyl]carbamate

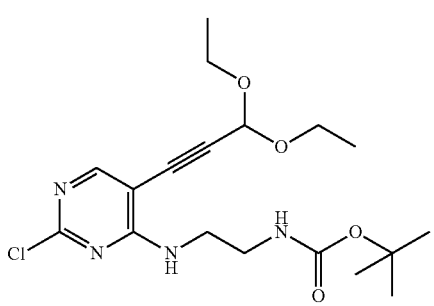 [SMILES: CCOC(C#Cc1cnc(Cl)nc1NCCNC(=O)OC(C)(C)C)OCC]

To tert-butyl N-[2-[(5-bromo-2-chloro-pyrimidin-4-yl)amino]ethyl]carbamate 5 g (14.23 mmole) in toluene (42 mL) and triethylamine (8.33 mL) under nitrogen was added triphenyl arsine (4.39 g), 3,3-diethoxyprop-1-yne (3.24 mL) and Pddba (1.27 g). The contents were heated at 70 degrees for 24 hrs. After filtration through celite, the crude reaction was columned using hexane/ethyl acetate (0-20%) to afford the desired product. 3.9 g. Column chromatography of the resulting residue using hexane/ethyl acetate (0-30%) afforded tert-butyl N-[2-[[2-chloro-5-(3,3-diethoxyprop-1-ynyl)pyrimidin-4-yl]amino]ethyl]carbamate. LCMS (ESI) 399 (M+H)

tert-butyl N-[2-[2-chloro-6-(diethoxymethyl)pyrrolo[2,3-d]pyrimidin-7-yl]ethyl]carbamate

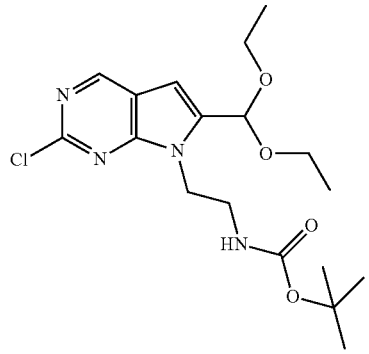 [SMILES: CCOC(OCC)c1cc2cnc(Cl)nc2n1CCNC(=O)OC(C)(C)C]

To a solution of the coupled product 3.9 g (0.00976 mole) in THF (60 mL) was added TBAF (68.3 mL, 7 eq). The contents were heated to 45 degrees for 2 hrs. Concentration followed by column chromatography using ethyl acetate/hexane (0-50%) afforded tert-butyl N-[2-[2-chloro-6-(diethoxymethyl)pyrrolo[2,3-d]pyrimidin-7-yl]ethyl]carbamate as a pale brown liquid (1.1 g). $^1$HNMR (d6-DMSO) 8.88 (s, 1H), 6.95 (brs, 1H), 6.69 (s, 1H), 5.79 (s, 1H), 4.29 (m, 2H), 3.59 (m, 4H), 3.34 (m, 1H), 3.18 (m, 1H), 1.19 (m, 9H), 1.17 (m, 6H). LCMS (ESI) 399 (M+H).

tert-butyl N-[2-[2-chloro-6-(diethoxymethyl)-5-iodo-pyrrolo[2,3-d]pyrimidin-7-yl]ethyl]carbamate

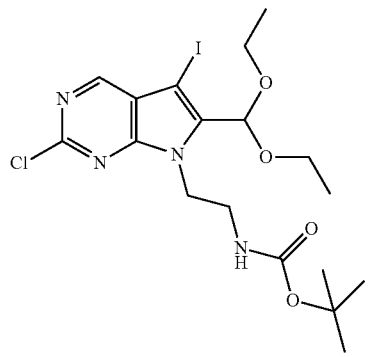 [SMILES: CCOC(OCC)c1c(I)c2cnc(Cl)nc2n1CCNC(=O)OC(C)(C)C]

To 0.1 g (0.00025 mole) of tert-butyl N-[2-[2-chloro-6-(diethoxymethyl)pyrrolo[2,3-d]pyrimidin-7-yl]ethyl]carbamate in acetonitrile (2 mL) was added 1,3-Diiodo-5,5-dimethylhydantoin (95 mg, 1 eq), and solid NaHCO$_3$ (63 mg, 3 eq). Stir at room temperature for 16 hrs. Filter, concentrate and then column with hexane/ethylacetate (0-50%) to afford tert-butyl N-[2-[2-chloro-6-(diethoxymethyl)-5-iodo-pyrrolo[2,3-d]pyrimidin-7-yl]ethyl]carbamate as a pale yellow solid 0.03 g. LCMS (ESI) 525 (M+H).

tert-butyl N-[2-[2-chloro-6-(diethoxymethyl)-5-(o-tolyl)pyrrolo[2,3-d]pyrimidin-7-yl]ethyl]carbamate

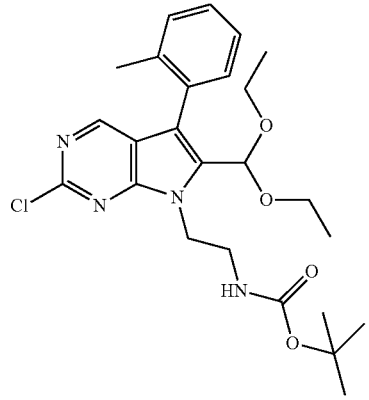 [SMILES: CCOC(OCC)c1c(-c2ccccc2C)c2cnc(Cl)nc2n1CCNC(=O)OC(C)(C)C]

To tert-butyl N-[2-[2-chloro-6-(diethoxymethyl)-5-iodo-pyrrolo[2,3-d]pyrimidin-7-yl]ethyl]carbamate (0.1 g, 0.19 mmole) in dioxane (3 mL) was added 2-Methylphenylboronic acid (28 mg), tetrakis(triphenylphosphine)palladium (25 mg) and 250 mg potassium phosphate in 0.3 mL water. Heat in a CEM Discovery microwave at 90° C. for 3 hrs. The crude reaction was loaded onto silica gel and columned using hexane/ethyl acetate (0-30%) to afford tert-butyl N-[2-[2-chloro-6-(diethoxymethyl)-5-(o-tolyl)pyrrolo[2,3-d]pyrimidin-7-yl]ethyl]carbamate (0.06 g). LCMS (ESI) 489 (M+H).

7-[2-(tert-butoxycarbonylamino)ethyl]-2-chloro-5-(o-tolyl)pyrrolo[2,3-d]pyrimidine-6-carboxylic acid

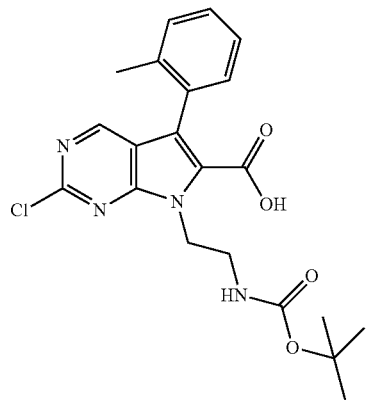 [SMILES: Cc1ccccc1-c1c(C(=O)O)n(CCNC(=O)OC(C)(C)C)c2nc(Cl)ncc12]

To tert-butyl N-[2-[2-chloro-6-(diethoxymethyl)-5-(o-tolyl)pyrrolo[2,3-d]pyrimidin-7-yl]ethyl]carbamate (0.85 g, 1.74 mmole) in AcOH (10 mL) was added water (1.5 mL), stir at room temperature for 16 hrs. The crude reaction was then concentrated under vacuum. After addition of ethyl acetate (50 mL) the organic layer was washed with satd. NaHCO$_3$. The organic layer was dried with magnesium sulfate and then concentrated under vacuum to afford the crude intermediate, tert-butyl N-[2-[2-chloro-6-formyl-5-(o-tolyl)pyrrolo[2,3-d]pyrimidin-7-yl]ethyl]carbamate. To this crude intermediate in DMF (5 mL) was added oxone (1.3 g). After stirring for 2.5 hrs, water (20 mL) and ethyl acetate (100 mL) was added. The organic layer was separated, dried and then concentrated under vacuum to afford the crude product which was columned over silica gel using hexane/ethyl acetate (0-50%) to afford 7-[2-(tert-butoxycarbonylamino)ethyl]-2-chloro-5-(o-tolyl)pyrrolo[2,3-d]pyrimidine-6-carboxylic acid (0.112 g). LCMS (ESI) 431 (M+H).

Intermediate (IN-1):

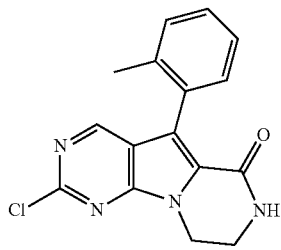

(IN-1)

To 0.1 g (0.261 mmole) of 7-[2-(tert-butoxycarbonylamino)ethyl]-2-chloro-5-(o-tolyl)pyrrolo[2,3-d]pyrimidine-6-carboxylic acid in DCM (4.1 mL) was added DMAP (20 mg) followed by the addition of N,N'-Diisopropylcarbodiimide (0.081 mL, 2 eq). After stirring for 3 hrs, TFA (0.723 mL) was added. Stirring was then continued for another 30 minutes. The reaction mixture was neutralized with satd. NaHCO3. DCM (20 mL) was then added and the organic layer separated, dried with magnesium sulfate and then concentrated under vacuum to afford the crude product which was columned using hexane/ethylacetate (0-100%) to afford chloro tricyclic amide Intermediate (IN-1)(0.65 g). LCMS (ESI) 313 (M+H).

Compound (1):

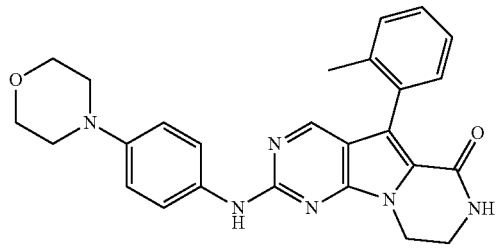

(1)

To 0.040 g (0.128 mmole) of the chloro tricyclic amide (IN-1) in dioxane (2.5 mL) under nitrogen was added Pd$_2$(dba)$_3$ (12 mg), sodium tert-butoxide (16 mg), BINAP (16 mg) 4-morpholinoaniline (22.7 mg, 1 eq). The reaction mixture was heated at 90° C. in a CEM Discovery microwave for 3.0 hrs. The crude reaction was loaded on a silica gel column and the contents eluted with DCM/MeOH (0-6%) to afford Compound (1) (10 mg). LCMS (ESI) 455 (M+H). 1H NMR (600 MHz, DMSO-d$_6$) d ppm 2.14 (s, 3H) 3.23-3.50 (m, 2H) 3.57-3.73 (m, 2H), 3.81-3.92 (m, 8H), 7.11-7.31 (m, 4H) 7.31-7.48 (m, 1H) 7.58-7.73 (m, 1H) 7.77-7.95 (m, 2H) 8.05-8.21 (m, 1H) 8.44 (s, 1H) 9.85-10.01 (m, 1H).

Compound (2):

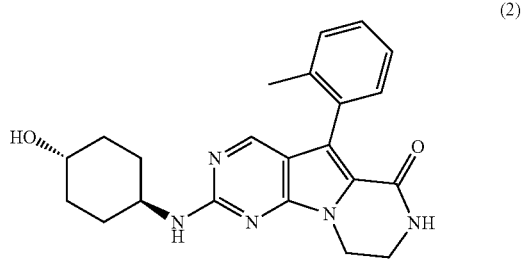

(2)

To 0.024 g of the chloro tricyclic amide (IN-1)) in N-methyl-2-pyrrolidone (NMP) (1.5 mL) was added trans-4-aminocyclohexanol (0.0768 mmol, 26.54 mg, 3 eq) and 0.4 mL Hunigs base. The reaction was heated in a CEM Discovery microwave vessel at 150 OC for 1.2 hrs. The crude reaction was loaded on a silica gel column and the contents eluted with DCM/MeOH (0-10%) to afford Compound (2) (21 mg). LCMS (ESI) 392 (M+H). 1H NMR (600 MHz, DMSO-d$_6$) d ppm 1.23 (d, J=8.78 Hz, 4H) 1.84 (br. s., 4H) 2.11 (s, 3H) 3.34-3.43 (m, 1H) 3.55 (br. s., 2H) 3.72 (br. s., 1H) 4.13 (br. s., 2H) 4.50 (br. s., 1H) 7.03 (br. s., 1H) 7.12-7.28 (m, 4H) 7.96 (br. s., 1H) 8.18 (br. s., 1H).

7-[2-(tert-butoxycarbonylamino)ethyl]-2-chloro-pyrrolo[2,3-d]pyrimidine-6-carboxylic acid

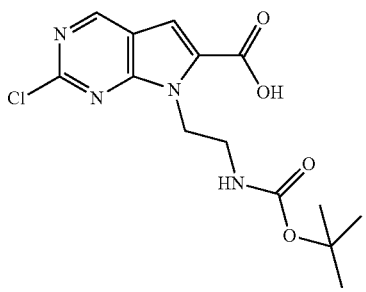 [SMILES: CC(C)(C)OC(=O)NCCn1c(C(=O)O)cc2cnc(Cl)nc21]

7-[2-(tert-butoxycarbonylamino)ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 341 (M+H).

Intermediate (IN-2):

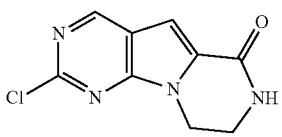

(IN-2)

Chloro tricyclic amide (IN-2) was synthesized using a similar experimental procedure as that described for the synthesis of chloro tricyclic amide (IN-1). LCMS (ESI) 223 (M+H)

Compound (3):

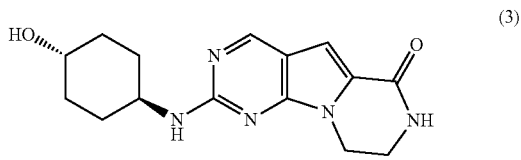

To the chloro tricyclic amide (IN-2) (0.035 g, 0.00157 mole) in NMP (1.5 mL) was added Hunigs base (0.3 mL) followed by the addition of the trans-4-aminocyclohexanol (54.2 mg). The reaction mixture was heated at 150° C. for 1.5 hrs. The crude reaction was loaded on a silica gel column and the contents eluted with DCM/MeOH (0-10%) to afford Compound (3) (5 mg). LCMS (ESI) 302 (M+H).

tert-butyl N-[2-[(5-bromo-2-chloro-pyrimidin-4-yl)amino]-2-methyl-propyl]carbamate

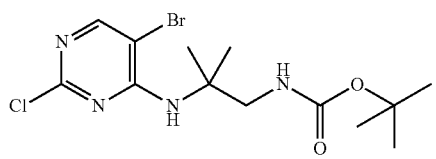 [SMILES: CC(C)(CNC(=O)OC(C)(C)C)Nc1nc(Cl)ncc1Br]

tert-butyl N-[2-[(5-bromo-2-chloro-pyrimidin-4-yl)amino]-2-methyl-propyl]carbamate is synthesized by treating 5-Bromo-2,4-dichloropyrimidine with tert-butyl N-(2-amino-2-methyl-propyl)carbamate using similar experimental conditions as described for the synthesis of tert-butyl N-[2-[(5-bromo-2-chloro-pyrimidin-4-yl)amino]ethyl]carbamate. LCMS (ESI) (M+H) 379 tert-butyl N-[2-[[2-chloro-5-(3,3-diethoxyprop-1-ynyl)pyrimidin-4-yl]amino]-2-methyl-propyl]carbamate

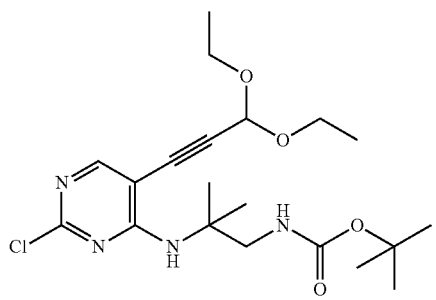 [SMILES: CCOC(C#Cc1cnc(Cl)nc1NC(C)(C)CNC(=O)OC(C)(C)C)OCC]

tert-butyl N-[2-[[2-chloro-5-(3,3-diethoxyprop-1-ynyl)pyrimidin-4-yl]amino]-2-methyl-propyl]carbamate is synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) (M+H) 427.

tert-butyl N-[2-[2-chloro-6-(diethoxymethyl)pyrrolo[2,3-d]pyrimidin-7-yl]-2-methyl-propyl]carbamate

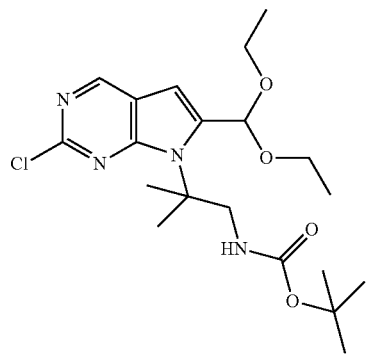 [SMILES: CCOC(OCC)c1cc2cnc(Cl)nc2n1C(C)(C)CNC(=O)OC(C)(C)C]

tert-butyl N-[2-[2-chloro-6-(diethoxymethyl)pyrrolo[2,3-d]pyrimidin-7-yl]-2-methyl-propyl]carbamate is synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3-d]pyrimidin-7-yl]ethyl]carbamate. LCMS (ESI) (M+H) 427

7-[2-(tert-butoxycarbonylamino)-1,1-dimethyl-ethyl]-2-chloro-pyrrolo[2,3-d]pyrimidine-6-carboxylic acid

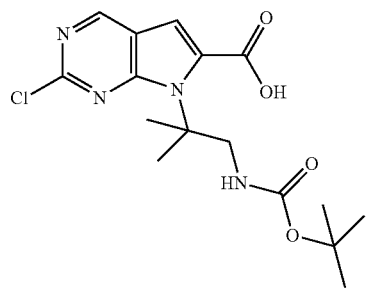 [SMILES: CC(C)(C)OC(=O)NCC(C)(C)n1c(C(=O)O)cc2cnc(Cl)nc21]

7-[2-(tert-butoxycarbonylamino)-1,1-dimethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 369 (M+H).

Intermediate (IN-3):

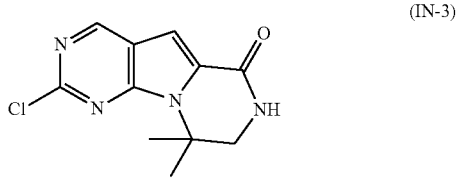

Chloro tricyclic amide (IN-3) was synthesized using a similar procedure as that described for the synthesis of chloro tricyclic amide Intermediate (IN-1). LCMS (ESI) 251 (M+H).

Compound (4):

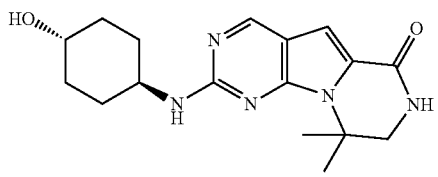

Compound (4) was synthesized by treating chlorotricyclic amine Intermediate (IN-3) with trans-4-aminocyclohexanol using similar experimental conditions as for compound (3). LCMS (ESI) 330 (M+H). 1H NMR (600 MHz, DMSO-$d_6$) d ppm 1.07-1.34 (m, 4H) 1.47-2.05 (m, 10H) 3.09 (m, 1H) 3.51 (d, J=2.91 Hz, 2H) 3.57 (m, 1H) 4.50 (br. s., 1H) 6.89 (s, 1H) 6.94-7.05 (m, 1H) 8.04 (br. s., 1H) 8.60 (s, 1H) 9.00 (br. s., 1H).

benzyl N-[1-[[(5-bromo-2-chloro-pyrimidin-4-yl)amino]methyl]propyl]carbamate

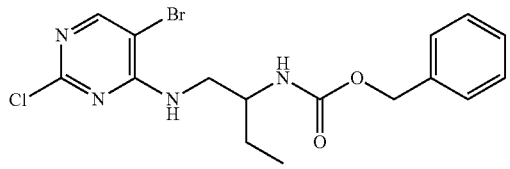 [SMILES: CCC(CNc1nc(Cl)ncc1Br)NC(=O)OCc1ccccc1]

benzyl N-[1-[[(5-bromo-2-chloro-pyrimidin-4-yl)amino]methyl]propyl]carbamate is synthesized by treating 5-Bromo-2,4-dichloropyrimidine with benzyl N-[1-(aminomethyl)propyl]carbamate using similar experimental conditions as described for the synthesis of tert-butyl N-[2-[(5-bromo-2-chloro-pyrimidin-4-yl)amino]ethyl]carbamate. LCMS (ESI) (M+H) 413 benzyl N-[1-[[[2-chloro-5-(3,3-diethoxyprop-1-ynyl)pyrimidin-4-yl]amino]methyl]propyl]carbamate

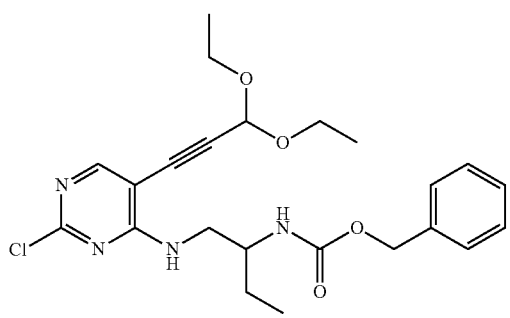 [SMILES: CCOC(C#Cc1cnc(Cl)nc1NCC(CC)NC(=O)OCc1ccccc1)OCC]

benzyl N-[1-[[[2-chloro-5-(3,3-diethoxyprop-1-ynyl)pyrimidin-4-yl]amino]methyl]propyl]carbamate is prepared by treating benzyl N-[1-[[(5-bromo-2-chloro-pyrimidin-4-yl)amino]methyl]propyl]-carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) (M+H) 461.

benzyl N-[1-[[2-chloro-6-(diethoxymethyl)pyrrolo[2,3-d]pyrimidin-7-yl]methyl]propyl]carbamate

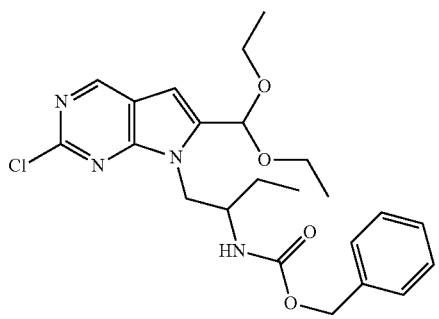 [SMILES: CCOC(OCC)c1cc2cnc(Cl)nc2n1CC(CC)NC(=O)OCc1ccccc1]

benzyl N-[1-[[2-chloro-6-(diethoxymethyl)pyrrolo[2,3-d]pyrimidin-7-yl]methyl]propyl]carbamate is synthesized by treating benzyl N-[1-[[[2-chloro-5-(3,3-diethoxyprop-1-ynyl)pyrimidin-4-yl]amino]methyl]propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) (M+H) 461

7-[2-(benzyloxycarbonylamino)butyl]-2-chloro-pyrrolo[2,3-d]pyrimidine-6-carboxylic acid

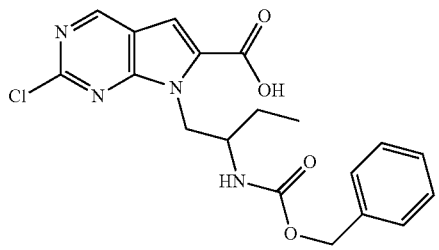 [SMILES: CCC(Cn1c(C(=O)O)cc2cnc(Cl)nc21)NC(=O)OCc1ccccc1]

7-[2-(benzyloxycarbonylamino)butyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 403 (M+H).

Intermediate (IN-4):

(IN-4)

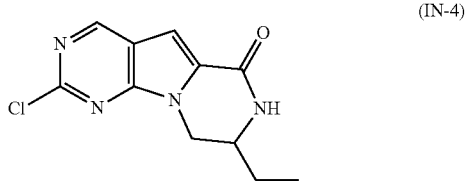

To a solution of 7-[2-(benzyloxycarbonylamino)butyl]-2-chloro-pyrrolo[2,3-d]pyrimidine-6-carboxylic acid in dichloromethane was added HBr, the reaction was stirred at 45 degrees for 3 hrs. After concentration, 2N NaOH was added to basify (pH=8.0) followed by the addition of THF (20 mL). Boc$_2$O was then added (1.2 eq) and then contents stirred for 16 hrs. To the crude reaction mixture was then added ethyl acetate (100 mL) and water (50 mL) and the organic phase was separated, dried (magnesium sulfate) and then conc under vacuum. To the crude product was added dichloromethane (30 mL) followed by DIC and DMAP. After stirring for 2 hrs, TFA was added and the contents stirred for an hour. The solvents were evaporated under vacuum and the residue basified with satd. NaHCO3. Ethyl acetate was then added and the organic layer separated, dried (magnesium sulfate) and then concentrated under vacuum. Column chromatography with hexane/ethyl acetate (0-100%) afforded the desired chlorotricyclic core Intermediate (IN-4). LCMS (ESI) 251 (M+H).

Compound (5):

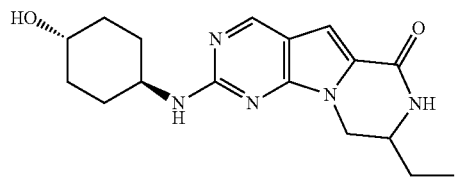

(5)

Compound (5) was synthesized by treating chlorotricyclic amine Intermediate (IN-4) with trans-4-aminocyclohexanol using similar experimental conditions as for compound (3). LCMS (ESI) 330 (M+H). 1H NMR (600 MHz, DMSO-d$_6$) ppm 0.80-0.95 (m, 3H) 1.35-1.92 (m, 10H) 3.66 (br. m., 3H) 4.17 (br. s., 2H) 4.47 (br. s., 1H) 6.85 (s, 1H) 6.96 (br. s., 1H) 8.15 (br. s., 1H) 8.62 (br. s., 1H).

tert-butyl N-[1-[[(5-bromo-2-chloro-pyrimidin-4-yl)amino]methyl]cyclopentyl]carbamate

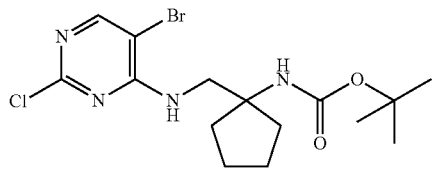 [SMILES: CC(C)(C)OC(=O)NC1(CNc2nc(Cl)ncc2Br)CCCC1]

tert-butyl N-[1-[[(5-bromo-2-chloro-pyrimidin-4-yl)amino]methyl]cyclopentyl]carbamate was synthesized by treating 5-bromo-2,4-dichloropyrimidine with tert-butyl N-[1-(aminomethyl)cyclopentyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H).

tert-butyl N-[1-[[[2-chloro-5-(3,3-diethoxyprop-1-ynyl)pyrimidin-4-yl]amino]methyl]cyclopentyl]carbamate

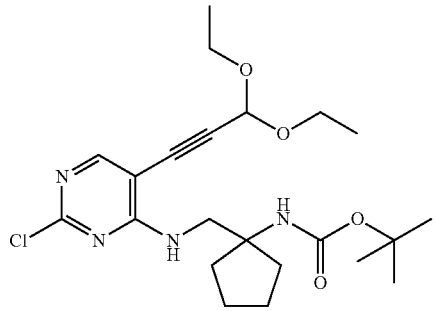 [SMILES: CCOC(C#Cc1cnc(Cl)nc1NCC1(NC(=O)OC(C)(C)C)CCCC1)OCC]

tert-butyl N-[1-[[[2-chloro-5-(3,3-diethoxyprop-1-ynyl)pyrimidin-4-yl]amino]methyl]cyclopentyl]carbamate was synthesized by treating tert-butyl N-[1-[[(5-bromo-2-chloro-pyrimidin-4-yl)amino]methyl]cyclopentyl]carbamate with with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate LCMS (ESI) 453 (M+H).

tert-butyl N-[1-[[2-chloro-6-(diethoxymethyl)pyrrolo[2,3-d]pyrimidin-7-yl]methyl]cyclopentyl]carbamate

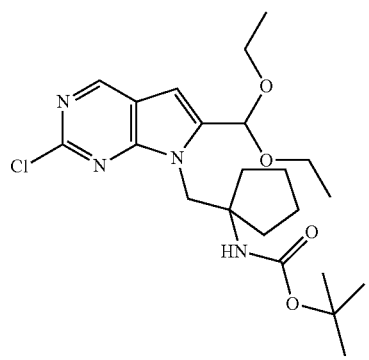 [SMILES: CCOC(OCC)c1cc2cnc(Cl)nc2n1CC1(NC(=O)OC(C)(C)C)CCCC1]

tert-butyl N-[1-[[2-chloro-6-(diethoxymethyl)pyrrolo[2,3-d]pyrimidin-7-yl]methyl]cyclopentyl]carbamate is synthesized by treating tert-butyl N-[2-[[2-chloro-5-(3,3-diethoxyprop-1-ynyl)pyrimidin-4-yl]amino]-2-methylpropyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 453 (M+H).

7-[[1-(tert-butoxycarbonylamino)cyclopentyl]methyl]-2-chloro-pyrrolo[2,3-d]pyrimidine-6-carboxylic acid

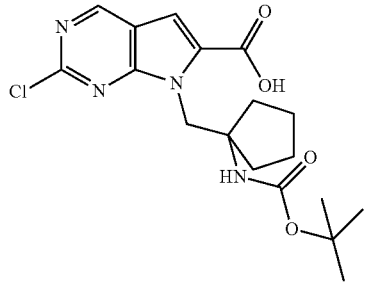 [SMILES: CC(C)(C)OC(=O)NC1(Cn2c(C(=O)O)cc3cnc(Cl)nc32)CCCC1]

7-[[1-(tert-butoxycarbonylamino)cyclopentyl]methyl]-2-chloro-pyrrolo[2,3-d]pyrimidine-6-carb oxylic acid was synthesized using a similar experimental procedure as that described for the synthesis of 7-[2-(tert-butoxycarbonylamino)ethyl]-2-chloro-5-(o-tolyl)pyrrolo[2,3-d]pyrimidine-6-carboxylic acid. LCMS (ESI) 395 (M+H).

Intermediate (IN-5):

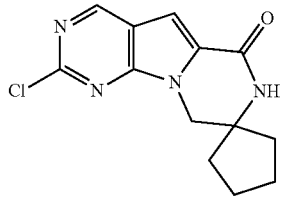

(IN-5)

Chlorotricyclic core Intermediate (IN-5) was synthesized using a similar experimental procedure as that described for the synthesis of chloro tricyclic amide (IN-1). LCMS (ESI) 277 (M+H).

Compound (6):

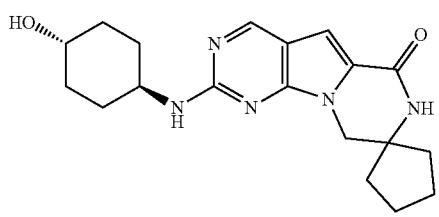

(6)

Compound (6) was synthesized by treating chlorotricyclic amine Intermediate (IN-5) with trans-4-aminocyclohexanol using similar experimental conditions as for compound (3). LCMS (ESI) 356 (M+H). 1H NMR (600 MHz, DMSO-$d_6$) d ppm 1.08-1.32 (m, 8H) 1.60-2.09 (m, 8H) 3.03-3.17 (m, 1H) 3.35 (s, 2H) 3.54-3.62 (m, 1H) 4.51 (d, J=4.39 Hz, 1H) 6.88 (s, 1H) 6.96 (br. s., 1H) 8.07 (br. s., 1H) 8.58 (s, 1H).

tert-butyl N-[[1-[(5-bromo-2-chloro-pyrimidin-4-yl)amino]cyclopentyl]methyl]carbamate

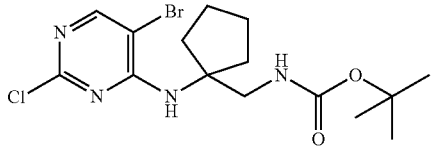 [SMILES: CC(C)(C)OC(=O)NCC1(Nc2nc(Cl)ncc2Br)CCCC1]

tert-butyl N-[[1-[(5-bromo-2-chloro-pyrimidin-4-yl)amino]cyclopentyl]methyl]carbamate is synthesized by treating 5-Bromo-2,4-dichloropyrimidine with tert-butyl N-[(1-aminocyclopentyl)methyl]carbamate using similar experimental conditions as described for the synthesis of tert-butyl N-[2-[(5-bromo-2-chloro-pyrimidin-4-yl)amino]ethyl]carbamate. LCMS (ESI) 405 (M+H)

tert-butyl N-[2-[[2-chloro-5-(3,3-diethoxyprop-1-ynyl)pyrimidin-4-yl]amino]-2-methyl-propyl]carbamate

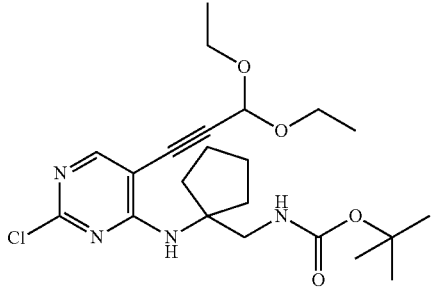 [SMILES: CCOC(C#Cc1cnc(Cl)nc1NC1(CNC(=O)OC(C)(C)C)CCCC1)OCC]

tert-butyl N-[[1-[[2-chloro-5-(3,3-diethoxyprop-1-ynyl)pyrimidin-4-yl]amino]cyclopentyl]methyl]carbamate is synthesized by treating tert-butyl N-[2-[(5-bromo-2-chloro-pyrimidin-4-yl)amino]-2-methyl-propyl]carbamate with 3,3-diethoxyprop-1-yne in the presence of a catalyst such as Pddba using similar experimental conditions as described for the synthesis of tert-butyl N-[2-[[2-chloro-5-(3,3-diethoxyprop-1-ynyl)pyrimidin-4 yl]amino]ethyl]carbamate. LCMS (ESI) 453 (M+H).

tert-butyl N-[[1-[2-chloro-6-(diethoxymethyl)pyrrolo[2,3-d]pyrimidin-7-yl]cyclopentyl]methyl]carbamate

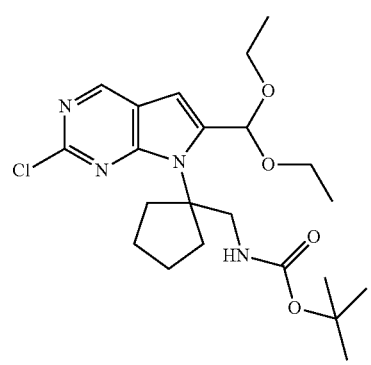 [SMILES: CCOC(OCC)c1cc2cnc(Cl)nc2n1C1(CNC(=O)OC(C)(C)C)CCCC1]

tert-butyl N-[[1-[2-chloro-6-(diethoxymethyl)pyrrolo[2,3-d]pyrimidin-7-yl]cyclopentyl]methyl]carbamate is synthesized by treating tert-butyl N-[2-[[2-chloro-5-(3,3-diethoxyprop-1-ynyl)pyrimidin-4-yl]amino]-2-methyl-propyl]carbamate with TBAF using similar experimental conditions as described for the synthesis tert-butyl N-[2-[2-chloro-6-(diethoxymethyl)pyrrolo[2,3 d]pyrimidin-7-yl]ethyl]carbamate. LCMS (ESI) 4534 (M+H).

7-[2-(tert-butoxycarbonylamino)-1,1-dimethyl-ethyl]-2-chloro-pyrrolo[2,3-d]pyrimidine-6carboxylic acid

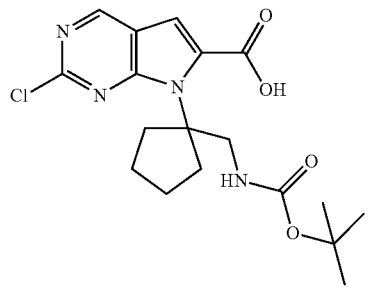 [SMILES: CC(C)(C)OC(=O)NCC1(n2c(C(=O)O)cc3cnc(Cl)nc32)CCCC1]

7-[2-(tert-butoxycarbonylamino)-1,1-dim ethyl-ethyl]-2-chloro-pyrrolo[2,3-d]pyrimidine-6-carboxylic acid was synthesized using a similar experimental procedure as that described for the synthesis of 7-[2-(tert-butoxycarbonylamino)ethyl]-2-chloro-5-(o-tolyl)pyrrol o[2,3-d]pyrimidine-6-carboxylic acid. LCMS (ESI) 395 (M+H)

Intermediate (IN-6): 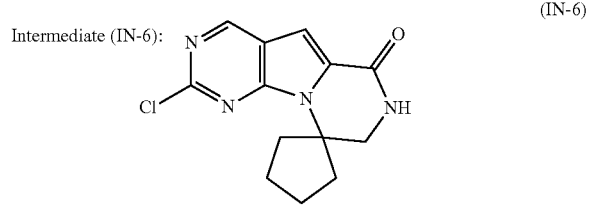 (IN-6)

Chloro tricyclic amide (IN-6) was synthesized using a similar experimental procedure as that described for the chloro tricyclic amide Intermediate (IN-1). LCMS (ESI) 277 (M+H).

Compound (7):

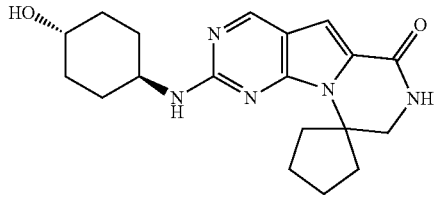 (7)

Compound (7) was synthesized by treating chlorotricyclic amine Intermediate (IN-6) with trans-4-aminocyclohexanol using similar experimental conditions as for compound (3). LCMS (ESI) 356 (M+H). 1H NMR (600 MHz, DMSO-$d_6$) d ppm 1.06-1.35 (m, 8H) 1.45-1.95 (m, 8H) 3.10 (m, 1H) 3.58 (br. s., 2H) 3.95 (br. s., 1H) 4.49 (br. s., 1H) 6.84 (s, 1H) 6.85-6.93 (m, 1H) 8.29 (s, 1H) 8.61 (br. s., 1H).

Each of Intermediates (IN-1) through (IN-6) and corresponding compounds with various $R^{27}$, $R^{31}$ and ZZ definitions may be reacted with sodium hydride and an alkyl halide or other halide to insert the desired $R^{26}$ substitution prior to reaction with an amine, such as described above for the synthesis of Compound (1), to produce the desired product of formulae (Q) or (QQ).

Biological Activity

Kinase activity is measured in vitro using electrophoretic mobility shift assay. The kinase reactions are assembled in 384 well plates in total volume of 25 µL. The reactions comprise: purified recombinant kinase enzyme, test compound, ATP (at apparent $K_m$ for each kinase), and fluorescently labeled peptide substrate. The reaction buffer composed of: 100 mM HEPES, pH7.5; 5 mM $MgCl_2$; 1 mM DTT; 0.1% bovine serum albumin; 0.01% Triton X-100, and 1% DMSO (from compound). The reactions were incubated at room temperature for indicated time and quenched by addition of 45 µL of termination buffer (100 mM HEPES pH7.5; 0.01% Triton X-100; 30 mM EDTA). Substrate and product peptides in each sample were electrophoretically separated and detected using 12 channel LabChip3000® microfluidic capillary electrophoresis instrument (Caliper Life Sciences). The change in the relative fluorescence intensities of substrate and product peaks (reflecting enzyme activity) was measured. Capillary electrophoregramms were analyzed using HTS Well Analyzer software (Caliper Life Sciences). The kinase activity in each sample was determined as "product to sum" ratio (PSR):P/(S+P), where P is the peak height of the product peptide and S is the peak height of the substrate peptide. Negative control samples (0%-inhibition in the absence of inhibitor) and positive control samples (100%-inhibition, in the presence of 20 mM EDTA) were assembled in replicates of four and were used to calculate %-inhibition values for each compound at each concentration. Percent inhibition ($P_{inh}$) was determined using following equation: $P_{inh}=(PSR_{0\%}-PSR_{inh})/(PSR_{0\%}-PSR_{100\%})*100$, where $PSR_{inh}$ is the product-sum ratio in the presence of inhibitor, $PSR_{0\%}$ is the average product-sum ration in the absence of inhibitor and $PSR_{100\%}$ is the average product-sum ratio in 100%-inhibition control samples. The IC50 values of reference inhibitors were determined by fitting the inhibition curves by a 4 parameter sigmoid dose-response model using XLfit 4 software (IDBS).

Activity of compounds of the invention is exemplified by the following test data:

| Kinase* | Compd 1 | Compd 2 | Compd 3 | Compd 4 | Compd 5 | Compd 6 | Compd 7 |
|---|---|---|---|---|---|---|---|
| Aurora -A | + | + | + | ++ | + | ++ | ++++ |
| DYRK3 | + | + | +++ | +++ | +++ | +++ | ++++ |
| FMS | + | + | + | ++++ | +++ | ++ | +++ |
| GSK-3 beta | + | + | +++ | ++++ | ++++ | ++++ | ++++ |
| HIPK4 | + | + | +++ | ++++ | ++++ | ++++ | ++++ |

-continued

| Kinase* | Compd 1 | Compd 2 | Compd 3 | Compd 4 | Compd 5 | Compd 6 | Compd 7 |
|---|---|---|---|---|---|---|---|
| JNK2 | + | +++ | ++++ | ++++ | ++++ | ++++ | ++++ |
| MAPK3 | + | ++ | +++ | +++ | +++ | ++++ | ++++ |
| MNK2 | + | + | + | +++ | ++ | ++ | +++ |
| P38 beta | + | + | + | ++ | ++ | ++ | +++ |

*Compounds tested at 10 μM concentration, activity is average of n = 2
+ <50%
++ 50-70%
+++ 71-90%
++++ >90%

Pharmaceutical Compositions

In one embodiment a pharmaceutical composition comprising one or more compounds of the invention is provided. In a first aspect, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, pharmaceutically acceptable salts and basic compounds such as free bases. A thorough discussion of pharmaceutically acceptable excipients and salts is available in Remington's Pharmaceutical Sciences, 18th Edition (Easton, Pa.: Mack Publishing Company, 1990). Depending on the intended mode of administration, the pharmaceutical composition may be in the form of solid, semi-solid or liquid dosage forms, such as, for example tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule non-aqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. A specific disease to be treated with compounds active against specific kinases is rheumatoid arthritis.

Multi-targeted approach to kinases is becoming an increasingly preferred approach for the treatment of inflammatory and cancer diseases to overcome resistance of single agent therapies. The present invention aims at combination therapy involving two or more protein kinase targets. For example, regorafenib, a multikinase inhibitor, given as a single agent to patients with treatment-refractory metastatic colorectal cancer, significantly improved overall survival and delayed disease progression in an international phase III trial.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:
1. A compound of formula (QQ):

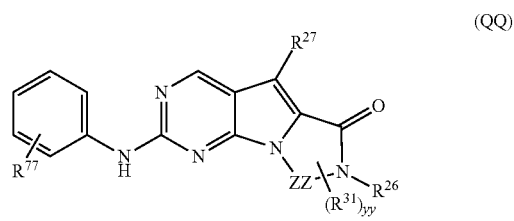

wherein
$R^{26}$ is H or $C_1$-$C_6$ alkyl;
$R^{27}$ is -(alkylene)$_m$-$C_3$-$C_8$ cycloalkyl or -(alkylene)$_m$-aryl; any of which may be optionally independently substituted with one or more $R^x$ groups as allowed by valance;

each $R^{31}$ is alkyl or two $R^{31}$s on adjacent ring atoms or on the same ring atom together with the ring atom(s) to which they are attached optionally form a 3-8-membered cycle;

yy is 0, 1, 2, 3, or 4;

ZZ is —$(CH_2)_{xx}$—, wherein xx is 1 or 2;

$R^{77}$ is -(alkylene)$_m$-heterocyclo or —(alkylene)$_m$-NR$^3$R$^4$, any of which may be optionally independently substituted with one or more $R^x$ groups as allowed by valance;

$R^3$ and $R^4$ at each occurrence are independently selected from:
(i) hydrogen, or
(ii) alkyl, heterocyclo, or heteroaryl;

$R^x$ at each occurrence is independently selected from halo, cyano, nitro, oxo, alkyl, haloalkyl, alkenyl, alkynyl, cycloalkyl, cycloalkenyl, heterocyclo, aryl, heteroaryl, arylalkyl, heteroarylalkyl, cycloalkylalkyl, and heterocycloalkyl, and m is 0 or 1.

2. The compound of claim 1, having the formula:

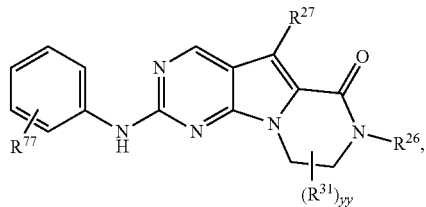

or a pharmaceutically acceptable salt thereof.

3. The compound of claim 1, having the formula:

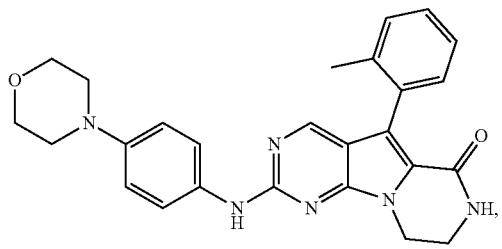 [SMILES: Cc1ccccc1-c1c2n(c3nc(Nc4ccc(N5CCOCC5)cc4)ncc13)CCNC2=O]

or a pharmaceutically acceptable salt thereof.

4. The compound of claim 1, wherein $R^{26}$ is selected from the group consisting of H, methyl, ethyl, n-propyl, and sec-butyl.

5. The compound of claim 1, wherein $R^{31}$ is selected from the group consisting of methyl, ethyl, n-propyl, and iso-propyl.

6. The compound of claim 1, wherein $R^{27}$ is selected from the group consisting of phenyl, ortho-methylphenyl, ortho, ortho-dimethylphenyl, para-ethylphenyl and ortho, para-dichlorophenyl.

7. The compound of claim 1, wherein yy is 0, 1 or 2.

8. The compound of claim 1, wherein $R^3$ and $R^4$ are independently selected from the group consisting of H, methyl, and ethyl.

9. The compound of claim 1, wherein $R^x$ is selected from the group consisting of chloro, methyl, ethyl, and cyclopentyl.

10. The compound of claim 1, wherein $R^{77}$ is selected from the group consisting of 1-morpholino, 2-methyl-1-morpholino, and 2,6-dimethyl-1-morpholino.

11. A pharmaceutical composition comprising an effective amount of the compound of claim 1, or a pharmaceutically acceptable salt thereof, and a pharmaceutically acceptable carrier.

12. The compound of claim 1, wherein $R^{27}$ is $C_3$-$C_8$ cycloalkyl or phenyl.

13. The compound of claim 12, wherein $R^{77}$ is heterocyclo.

14. The compound of claim 13, wherein heterocyclo is piperazine.

15. The compound of claim 12, wherein m is 0 and $R^{77}$ is heterocyclo substituted with one $R^x$ group.

16. The compound of claim 15, wherein heterocyclo is piperazine and $R^x$ is alkyl.

17. The compound of claim 16, wherein yy is 2 and xx is 2.

18. The compound of claim 17, wherein two $R^{31}$s on the same ring atom together with the ring atom to which they are attached form a 3-8-membered cycle.

19. The compound of claim 18, wherein the 3-8-membered cycle is a 6 membered cycle.

20. The compound of claim 19, wherein $R^{26}$ is H.

* * * * *